US010113956B1

United States Patent
Li et al.

(10) Patent No.: US 10,113,956 B1
(45) Date of Patent: Oct. 30, 2018

(54) REMOTE GAS LEAKAGE DETECTION SYSTEMS USING MID-INFRARED LASER

(71) Applicant: AnkhWiz Solutions LLC, Missouri City, TX (US)

(72) Inventors: Jiebo Li, Pearland, TX (US); Xunmin Guo, Fulshear, TX (US); Wanyi Zhao, Missouri City, TX (US)

(73) Assignee: Aurora Innovative Technology LLC, Missouri City, TX (US)

( * ) Notice: Subject to any disclaimer, the term of this patent is extended or adjusted under 35 U.S.C. 154(b) by 0 days.

(21) Appl. No.: 15/678,052

(22) Filed: Aug. 15, 2017

(51) Int. Cl.
*G01J 5/02* (2006.01)
*G01N 21/3504* (2014.01)
*G01N 21/39* (2006.01)
*B64C 39/02* (2006.01)
*G01N 21/61* (2006.01)
*G01N 33/00* (2006.01)

(52) U.S. Cl.
CPC ......... *G01N 21/3504* (2013.01); *B64C 39/02* (2013.01); *G01N 21/39* (2013.01); *G01N 21/61* (2013.01); *G01N 33/0027* (2013.01)

(58) Field of Classification Search
CPC ........ G01M 3/002; G01M 3/007; G01M 3/22; G01M 3/38; G01N 21/1702; G01N 21/3504; G01N 21/61; G05D 23/1917
See application file for complete search history.

(56) References Cited

U.S. PATENT DOCUMENTS

| | | | | |
|---|---|---|---|---|
| 5,430,293 | A * | 7/1995 | Sato | G01M 3/38 250/330 |
| 6,155,160 | A * | 12/2000 | Hochbrueckner | G05D 23/1917 126/112 |
| 7,075,653 | B1 * | 7/2006 | Rutherford | G01F 23/14 250/338.5 |
| 8,345,250 | B1 * | 1/2013 | Janosky | G01S 17/87 250/338.5 |
| 2004/0263852 | A1 * | 12/2004 | Degtiarev | G01M 3/38 356/437 |
| 2008/0277586 | A1 * | 11/2008 | Cardinale | G01M 3/002 250/339.13 |

* cited by examiner

*Primary Examiner* — Kiho Kim
(74) *Attorney, Agent, or Firm* — Fenwick & West LLP

(57) ABSTRACT

A system remotely detects a gas leakage from a target in an area. The gas detection system includes two light sources: a mid-infrared (mid-IR) laser for detecting absorbance of the gas in the area, and a visible laser for detecting a pathlength of the mid-IR laser. The absorption is determined based on the relative amplitude difference of the emitted and reflected mid-IR light beams. The mid-IR laser may use wavelength modulation techniques to improve the absorption determination. The pathlength is determined by comparing a phase between the emitted visible light beam and the measured visible light beam. The gas detection system calculates a concentration of the gas in the area using the determined absorption and pathlength. The gas detection system may be attached to an unmanned aerial vehicle.

20 Claims, 4 Drawing Sheets

REMOTE GAS LEAKAGE DETECTION SYSTEMS USING MID-INFRARED LASER

BACKGROUND OF THE INVENTION

1. Field of the Invention

This description relates generally to detection of gas leakage, and more specifically detection of gas leakage using mid-infrared laser.

2. Description of the Related Art

Natural gas consumption in the US is expected to increase rapidly. However, at the same time, gas delivery infrastructure is aging. Accordingly, reliable and timely detection of natural gas leakage is critical to ensure the gas delivery infrastructure's reliability. Conventional non-optical methods that detect natural gas leakage are based on various mechanisms such as manual inspection, acoustic monitoring; gas sampling; soil monitoring; flow monitoring; and software based dynamic modeling. However, these detection methods are often unreliable, inefficient, and expensive.

SUMMARY OF THE INVENTION

Described is a gas detection system for remotely detecting gas leakage from a target in an area. The gas detection system uses mid-infrared (mid-IR) laser for detecting gas leakage. The gas detection system also calculates a concentration of the leaked gas in the area by determining an absorption of the mid-IR laser by the leaked gas and a pathlength of the mid-IR laser. To determine the absorption by the gas in the area, the gas detection system emits a light beam in the mid-IR wavelength range (2-10 micrometers) and observes the reflected light beam. In some embodiments, the mid-IR light beam continuously sweeps through a range of wavelengths. The mid-IR light beam may be modulated as it sweeps through the range of wavelengths. The gas detection system determines the pathlength by emitting another light beam in the visible wavelength range and observing the reflected light beam. The gas detection system can be attached to an unmanned aerial vehicle or other moving carrier.

BRIEF DESCRIPTION OF THE DRAWINGS

The invention has other advantages and features which will be more readily apparent from the following detailed description of the invention and the appended claims, when taken in conjunction with the accompanying drawings, in which:

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
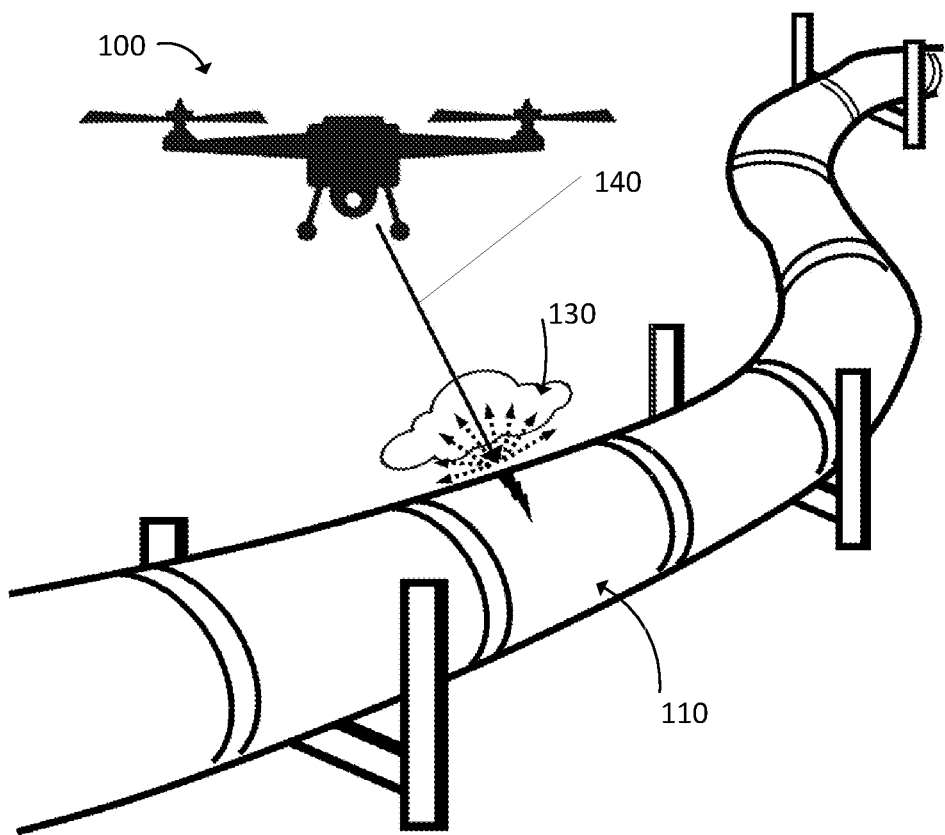
FIG. 1 illustrates an example environment in which an example gas detection system operates.

FIG. 1 illustrates an example environment in which an example gas detection system 100 operates. The example gas detection system 100 can remotely detect whether a gas pipe 110 has any gas leakage. In one example, the gas detection system can remotely detect gas leakage at a range of up to 50 meters. The detection system 100 detects gas leakage by detecting whether there is leaked gas in an area 130 that is between the detection system 100 and the gas pipe 110. As further described below, the detection system 100 projects one or more light beams 140 towards the gas pipe 110 while traversing along the gas pipe 110. The light beams 140 have wavelengths that are in the mid-infrared (IR) range (i.e., 2-10 ums (micrometers)). By collecting and analyzing light beams reflected by the gas pipe 110, the detection system 110 detects leaked gas in the area 130 thereby to detect gas leakage. As illustrated, the example detection system 100 includes an unmanned aerial vehicle (UAV) that flies along the gas pipe 110. A detection system can also be a stand-alone device that can be carried by a human or be attached to other types of instruments such as a hand-held mount, a balloon, a robot, an autonomous vehicle, and the like.

Figure 2:
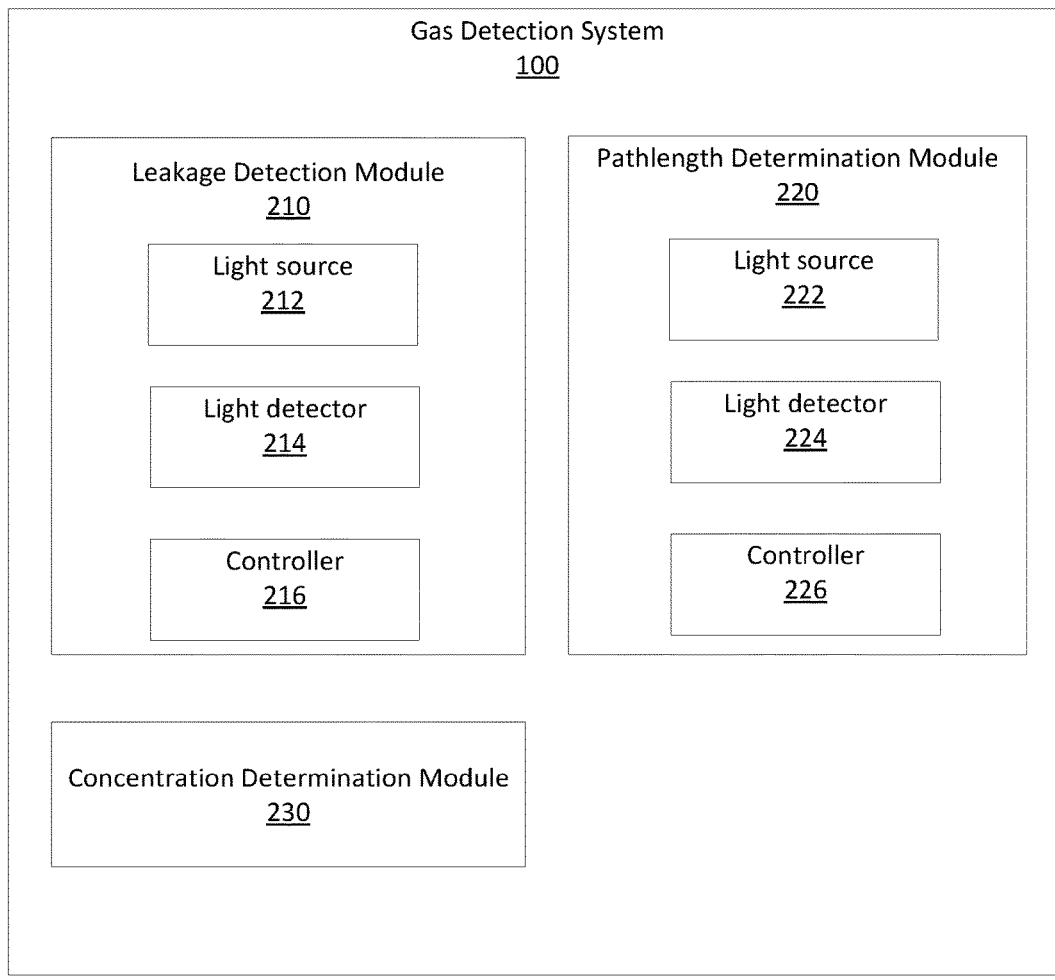
FIG. 2 illustrates an example gas detection system, according to one embodiment.

FIG. 2 illustrates an example gas detection system, according to one embodiment. The illustrated gas detection system 100 detects gas leakage by detecting the presence of one or more substances in an area between the gas detection system and a pipe or other conduits for transporting natural gas. The gas detection system 100 can additionally determine a concentration of the one or more substances in the area. The example gas detection system 100 includes a leakage detection module 210, a pathlength determination module 220, and a concertation determination module 230, all of which are further described below. As described herein, modules refers to hardware components, software components, and/or computational logic for providing functionality to gas detection systems. That is, a module can be implemented in hardware, mechanical elements, firmware, and/or software (e.g., a hardware server comprising computational logic), other embodiments can include additional modules, can distribute functionality between modules, can attribute functionality to more or fewer modules, can be implemented as a standalone program or as part of a network of programs, and can be loaded into memory executable by processors.

The leakage detection module 210 detects whether an area includes leaked gas. The leakage detection module 210 makes the detection by determination absorption of light beams by one or more substances in the area. The leakage detection module 210 emits light in a direction towards a region of a gas pipe to be inspected. The emitted light traverses an area towards the region of the gas pipe. An outer surface of the region of the gas pipe reflects the light emitted by the leakage detection module 210. The reflection can be diffuse reflection or specular reflection. The reflected light traverses the area towards the gas detection system 100. If the inspected region has a leakage, gas leaks into the area where the emitted light and the reflected light traverse. The leaked gas includes a substance that absorbs the emitted light and the reflected light. By detecting absorption of the reflected light by a substance, the leakage detection module 210 can determine whether the region has any leakage. A substance can be methane, ethane, ammonia, ethylene, propane, hydrocarbons, volatile organic compounds, or any other hazardous gas, etc.

The illustrated leakage detection module 210 includes a light source 212, a light detector 214, and a controller 216 that is coupled to the light source 212 and the light detector 214. The light source 212 emits a light beam having a set of light beam characteristics. Example light beam characteristics include a spot size, wavelength, intensity, directionality, polarization, and coherence (temporal and spatial). One or more light beam characteristics can be predetermined or configurable by the controller 216 as further described below. In various embodiments, the light source 212 includes one or more laser sources that generate one or more light beams having wavelengths in the mid-IR range. A light beam having a wavelength in the mid-IR range is hereinafter referred to as "the mid-IR light beam." The light source 212 may further include focusing optics and/or an optical fiber. The wavelength of the light emitted by the light source 212 is selected according to the substance of interest, because a particular substance absorbs light of different wavelengths at different rates. In one embodiment, the wavelength of the mid-IR light beam is selected to detect one substance. For example, a wavelength is selected to detect only methane. In another embodiment, the wavelength of the mid-IR light beam is selected to detect multiple substances. For example, a wavelength is selected to detect both methane and ethane.

In some embodiments, the gas detection system can be configured to detect multiple substances. For example, the wavelength of the mid-IR light beam can be tuned when detecting one of each of the multiple substances (e.g., emitting light of a first wavelength for detecting the first substance, emitting light of a second wavelength for detecting the second substance, etc.). This can be achieved by regulating a first laser source to emit light of the first wavelength and a second laser source to emit light of the second wavelength. The first and second laser sources can be regulated to emit light concurrently or separately. The wavelength of the mid-IR light beam can be tuned at startup of the gas detection system 100, remotely by an operator, or by accessing instructions stored on the system controller 216.

In some embodiments, the gas detection system 100 is based on the principle of tunable diode laser absorption spectroscopy (TDLAS). The gas detection system 100 tunes a wavelength of emitted light. The wavelength can be tuned by adjusting a temperature and/or an injection current density of the light source 212. The gas detection system 100 can also be based on the principle of wavelength modulation spectroscopy to detect a leakage of the substance in the area. A wavelength is modulated at a modulation signal at a higher frequency (e.g., a sinusoidal modulation signal at 10 kHz). The gas detection system 100 detects a harmonic (e.g., a first harmonic, a second harmonic) of the reflected signal and analyzes the detected harmonic to determine the absorption rate. That is, an intensity of the wavelength can be determined from the detected harmonic thereby to determine the absorption rate as described herein. The wavelength of the light source 212 may be continuously scanned across a range of wavelengths concurrently when the wavelength is modulated using the modulation signal. For example, the wavelength is continuously scanned from the wavelengths of 3245 nm to 3255 nm when the wavelength is modulated using the sinusoidal modulation signal at 10 k Hz. The leakage detection module 210 detects the absorption signal at the second harmonic of the modulation frequency which is at 20 kHz. The detected signal is analyzed to determine absorption rates of light at different wavelengths.

The focusing optics focuses the mid-IR light beam generated by the light source 212. For example, the focusing optics focus the mid-IR light beam at a point in the area. The mid-IR light beam diverges after that point and passes through the gas. In another embodiment, the mid-IR light beam diverges when emitted from the focusing optics. The divergence of the mid-IR light beam is related to the spot size of the emitted mid-IR light beam. The focusing optics can also modify the mid-IR light beam characteristics before the light beam exits the gas detection system 100. The focusing optics may include one or more optical elements such as a series of lenses, a collimator, wave plates, pinholes, filters, or any other optical elements. The focusing optics can be coupled to the laser source directly or via an optical fiber. The optical fiber transmits the mid-IR light beam emitted by the laser source to the focusing optics. The optical fiber can be a fiber-optic cable, a single mode fiber, a multi-mode fiber, or any other type of optically conductive fiber.

The light detector 214 captures incoming light and outputs signals representing intensity of the captured light. The controller 216 regulates the light detector 214 to capture light that is emitted by the light source 212 and reflected by the region of the gas pipe that is being inspected. The light detector 214 includes one or more photodetectors that detect photons and generate electrical signals in response to the detected photons. The photodetector can be any type of photodetector such as a photoelectric detector, an infrared photodetector, a semiconductor photodetector, a photovoltaic photodetector, or any other photodetector that can measure the intensity of the collected light. For example, the photodetector is an HgCdTe detector or a PdSe detector.

The light detector 214 may additionally include collection optics, an optical filter, and/or an amplifier. The collection optics collect incoming light from the region of the gas pipe that is being inspected. The collection optics has a focus length such that the collected light are focused onto the photodetectors. In some embodiments, the collection optics include a Fresnel lens.

The optical filter allows reflected light based on the light emitted by the light source 212 to pass and removes other light collected by the collection optics that have wavelengths outside the mid-IR range. Broadly, the optical filter removes ambient light (i.e., light that is undesirable for the detection of the substance). The filtered light is directed to the photodetector. In one example embodiment, the optical filter includes a band-pass filter that allows light having wavelengths in the range of 3200-3300 nm to pass. In other examples, the band-pass filter can include any range of wavelengths between 2-10 ums (i.e., mid-IR range) to pass. In some embodiments, the wavelength range of the light removed by the optical filters can be configured and adjusted. The optical filer is coupled to the collection optics and the one or more photodetectors. The optical filter can be a color filter, a neutral density filter, an optical low pass filter, or any other type of optical filter. The amplifier is coupled to the one or more photodetectors and amplifies the output of the photodetectors.

The leakage detection module 210 calculates an absorption rate indicating an amount of attenuation of the emitted light by the substance when the emitted light traversing the area. The absorption rate is determined by comparing the intensity of the outgoing mid-IR light beam of a particular wavelength emitted by the light source 212 to the intensity of the incoming mid-IR light beam of the particular wavelength collected by the light detector 214. Along the light path of the outgoing light emitted by the light source, the outgoing light is attenuated by the substance, reflected by the outer surface of the gas pipe, and further attenuated by the substance before being collected by the light detector 214. Accordingly, the calculated absorption rate accounts for both occurrences of absorption along the light path.

In some embodiments where the emitted signals are modulated, the leakage detection module 214 analyzes the reflected mid-IR light beam in reference to the modulation signal to determine the absorption rate of the gas in the area. The leakage detection module 214 may include a phase lock circuit to facilitate the analysis. The phase lock circuit minimizes the phase difference between the reflected mid-IR light beam and the modulation signal.

The leakage detection module 210 compares the determined absorption rate to a threshold to determine whether the region being inspected has a leakage. For a region that is being inspected, the leakage detection module 210 may calculate multiple absorption rates by emitting light beams along different directions toward the region. When the determined absorption rate is above a threshold value, the leakage detection module 210 determines that the region has a leakage. The leakage detection module 210 alerts a user accordingly. As an example, the leakage detection module alerts the user of the presence of methane if the absorption is greater than 0.05 meter parts per million (ppm·m). The leakage detection module 210 may record the location of the region being inspected. In further embodiments, the detection module 210 records a leaking location within the region being inspected that has the leakage. The leaking location is a location in the region that corresponds to a highest absorption rate determined.

The controller 216 determines and adjusts light beam characteristics of the mid-IR light beam emitted by the light source 212. The one or more light beam characteristics can be determined, for example, based on a distance of the gas detection system 100 from the region that is being inspected, a signal-to-noise ratio of the collected light, an ambient temperature, and the like. In some embodiments, the controller 216 adjusts a light beam size of the emitted mid-IR light beam. The controller 216 regulates the light source 212 to scan a region that is being inspected using a mid-IR light beam having a first light beam size. If the leakage detection module 210 determines that the region has a leakage. The controller 216 regulates the light source 212 to emit light have a second light beam size that is smaller than the first light beam size to confirm the detection of the leakage. As such, a false-alarm rate of detection of gas leakage is reduced. The controller 216 can further adjust the light source 212 to emit a mid-IR light beam that focuses on a leaking location within the particular region that is determined to have the leakage. In various embodiments, the first light beam size is in the range of 20-500 mm in diameter and the second light beam size is in the range of 6-20 mm in diameter.

In one embodiment, the controller 216 determines the wavelength of the mid-IR light beam for detecting a particular substance. The controller 216 selects the wavelength such that the emitted mid-IR light beam has the highest absorption rate by the substance among a range of wavelengths and that the emitted mid-IR light beam is not absorbed by other substances that may be in the area.

In one embodiment, the controller 216 determines the wavelength of the mid-IR light beam. In these cases, the wavelength of the mid-IR light beam is dependent on the drive current and temperature of the laser source. As an example, the emitted wavelength of the mid-IR light beam is 3058 $cm^{-1}$ when the drive current is 20 mA and the temperature of the laser source is 19° C. In a different example, the emitted wavelength of the mid-IR light beam is 3059 $cm^{-1}$ when the drive current is 32 mA and the temperature of the laser source is 11° C.

Additionally, in one embodiment, the controller 216 can determine the emitted optical power of the mid-IR light beam. In these cases, the emitted optical power of the mid-IR light beam is dependent on the input power (e.g., voltage and drive current) of the laser source (e.g., a distributed feedback interband cascade laser). As an example, the emitted optical power of the mid-IR light beam is 6 mW when the drive current is 50 mA and the applied voltage is 6.5 V. In a different example, the emitted optical power of the mid-IR light beam is 2 mW when the drive current is 30 mA and the applied voltage is 2.0 V.

The pathlength determination module 220 determines a pathlength of the light beam emitted by the light source 212. The pathlength determination module 220 emits another light beam towards the area that is being inspected and determines its pathlength. Because this light beam emitted by the pathlength determination module 220 and the light beam emitted by the light source 212 traverse substantially the same path, their pathlengths are substantially equal. The pathlength determination module 220 includes a light source 222, a light detector 224, and a controller 226 coupled to the light source 222 and the light detector 224. The light source 222 and the light detector 224 have similar functionalities and components as the light source 212 and the light detector 214, respectively. The controller 226 can also include wavelength modulation techniques as described above. Accordingly, description of the light source 222 and the light detector 224 similar to the light source 212 and the light detector 214 is omitted herein. In various embodiments, the light source 222 emits visible light (i.e., light having a wavelength in the range of 400-700 nm.) This light beam is hereinafter referred to as "the visible light beam." Visible light is unlikely to be absorbed by leaked gas and thus the pathlength can be more accurately determined by using visible light. The visible light can also be used to indicate the gas detection system 100. The controller 226 regulates the light source 222 to emit a visible light beam having a set of light beam characteristics. The controller regulates the light detector 224 to detect the incoming light beam that is the visible light beam emitted by the light source 222 being reflected by the gas pipe.

The pathlength determination module 220 analyzes light beam characteristics of the reflected visible light beam that is collected to determine the pathlength. The pathlength determination module 220 compares a phase of the collected visible light beam relative to that of the visible light beam emitted by the light source 212 to determine a phase difference thereby to determine how long it takes the emitted light beam to traverse the light path. For example, the pathlength determination module 220 compares the temporal coherence between the emitted and the collected visible light beams. For a region that is being inspected, the pathlength determination module 220 may calculate multiple pathlengths by emitting light beams toward the region along different directions. These calculated pathlengths correspond to the multiple absorption rates calculated by the leakage detection module 210.

In some embodiments, for a particular region that is being inspected, the pathlength determination module 220 determines the pathlength if the leakage detection module 210 determines that the region has a leakage. In some embodiments, for a particular region that is being inspected, the pathlength determination module 220 determines the pathlength concurrently with the leakage detection module 210 determining whether the region has a leakage. In some embodiments, the controller 216 and the controller 226 are implemented by a same controller. This controller may further determine a region to be inspected and/or an operation route that is the route the gas detection system 100 follows to track the gas pipe.

The concentration determination module 230 calculates a concentration of the substance in the area. The concentration detection module 230 receives the absorption rate determined by the leakage detection module 210 and the pathlength determined by the pathlength determination module 220, and calculates the concentration of the substance according to equation (1):

$$A = \varepsilon \cdot L \cdot C \qquad (1),$$

where A is the absorption rate of the light beam by a particular substance, ε is the molar absorptivity of the substance, L is the pathlength of the light beam as it traverses the area, and C is the concentration of the substance. For a region that is being inspected, the concentration determination module 230 may calculate multiple concentration values corresponding to different locations within the region. Each location corresponds to a direction of the light emitted by the leakage detection module 210. The gas detection system 100 outputs the determined concentration value to a user. The concentration determination module 230 may calculate the concentration if the leakage detection module 210 detects that there is a gas leakage. Alternatively, the concentration determination module 230 calculates the concentration concurrently with the leakage detection module 210 detecting whether there is a gas leakage.

In one embodiment, the concentration determination module 230 calculates the concentration of the substance using regression analysis. The measured absorption signal of the incoming mid-IR light beam is measured at a second harmonic of the modulation frequency of the emitted mid-IR light beam. The concentration is proportional to the second derivative of the of the absorption signal.

In some embodiments, the pathlength determination module 220 determines the pathlength if the leakage detection module 210 determines that there is a leakage. In some embodiments, the pathlength determination module 220 determines the pathlength concurrently with the leakage detection module 210 determining whether there is a leakage.

The gas detection system 100 may further include one or more other modules such as a locomotion module, a power module, an interface module, and a communication module. The locomotion module controls the movement of the gas detection system 100. The power module includes a battery pack and/or a protection circuit module as well as a power management system. Importantly, the power module powers the various components of the detector system 100 during operation. The interface module provides I/O functionality including user interfaces, data acquisition modules, USB interfaces, network interfaces, or any other input or output device that can be used to interact with and control the gas detection system 100. The communication module includes a wireless communication system that is based on various communication protocols such as long term evolution (LTE), 3G, 4G, and/or 5G mobile communication standards.

Compared to using near-IR light to detect gas leakage, embodiments described herein using mid-IR light to detect gas leakage more accurately, more reliably, more quickly, and with a higher sensitivity. Various embodiments described herein can detect leaked gas at a much lower concentration than conventional systems. For example, one embodiment can detect leaked methane in the order of 0.05 meter parts per million (ppm·m).

Figure 3:
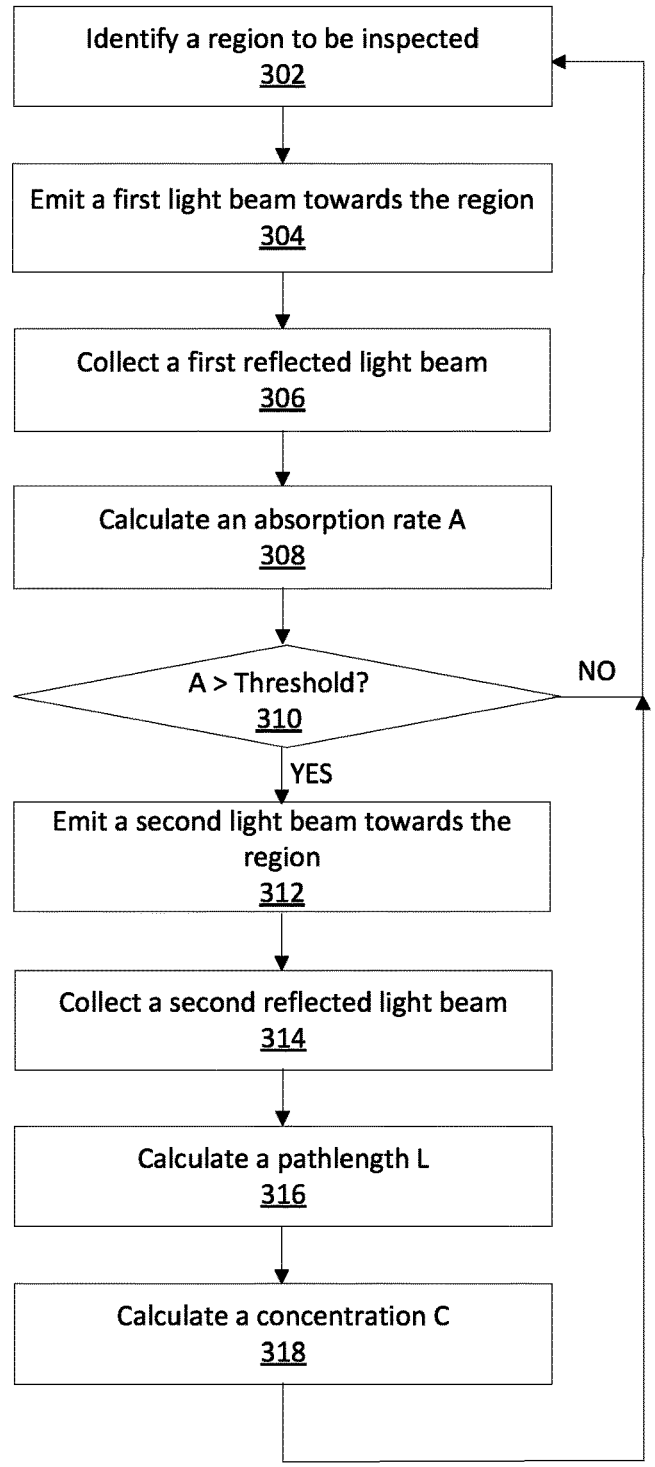
FIG. 3 is a flow chart illustrating an example process of detecting gas leakage, according to one embodiment.

FIG. 3 is a flow chart illustrating an example process of detecting gas leakage, according to one embodiment. The gas detection system identifies 302 a region of a gas pipe to be inspected. The gas detection system inspects a region of the gas pipe at a particular time point as it traverses along the gas pipe. A dimension of a region inspected at a time point can be predetermined by a user or determined by the gas detection system according to the ambient environment. In some embodiments, the regions are selected such that there is no gap between any two consecutive regions such that the gas detection system can inspect the gas pipe entirely or substantially entirely.

The gas detection system emits 304 a mid-IR light beam towards the region. The mid-IR light beam has a wavelength that is in the mid-IR range. The wavelength can be predetermined or determined based on the substance of interest. Other light beam characteristics of the first light beam can also be predetermined or determined by the gas detection system as described above with reference to FIG. 2. In some embodiments, the gas detection system emits multiple light beams along different directions towards the region either concurrently or sequentially. These light beams are incident on different locations within the region. This way, the gas detection system can inspect the different locations within the region.

The gas detection system collects 306 a first reflected light beam which is the first light beam emitted by the gas detection system reflected off of an outer surface of the region that is being inspected. The gas detection system calculates 308 an absorption rate of the first light beam by a substance in an area between the gas detection system and the region being inspected using the first emitted light beam and the first reflected light beam. For example, the gas detection system compares an intensity of the first emitted light beam to an intensity of the first reflected light beam to calculate the absorption rate. In some embodiments, for the region, the gas detection system calculates multiple absorption rates corresponding to the different locations of the region. The gas detection system compares 310 the calculated absorption rate to a threshold absorption rate. If the calculated absorption rate is less than the threshold, the gas detection system selects a next region to be inspected. If the calculated absorption rate is above the threshold, the gas detection system determines that the region being inspected has a leakage. In some embodiments, the gas detection system decreases a beam spot size of the first light beam and re-calculates the absorption rate to confirm that the region being inspected has a leakage.

Subsequently, the gas detection system emits 312 a second light beam towards the region that is being inspected. The second light beam has a second wavelength that is in the visible-light range. The gas detection system collects 314 a second reflected light beam which is the second light beam emitted by the gas detection system reflected off of the outer surface of the region that is being inspected. The gas detection system calculates 316 a pathlength of the first light beam using the second emitted light beam and the second reflected light beam. For example, the gas detection system determines a phase difference between the second emitted light beam and the second reflected light beam to calculate the pathlength. The gas detection system calculates 318 a concentration of the substance in the area between the gas detection system and the gas pipe using the determined absorption rate and the pathlength. The gas detection system transitions to inspect a next region. In some embodiments, the gas detection system can emit multiple second light beams along different directions towards the region, and calculates multiple pathlengths and/or concentration along those different directions, either sequentially or concurrently.

In the illustrated example, the gas detection system emits the second light beam thereby to calculate the pathlength and the concentration if it detects there is a gas leakage. In other embodiments, the gas detection system concurrently emits the first and second light beams, concurrently calculates the absorption rate and the pathlength. In further embodiments, the gas detection system concurrently calculates the absorption rate, the pathlength, and the concentration.

Figure 4:
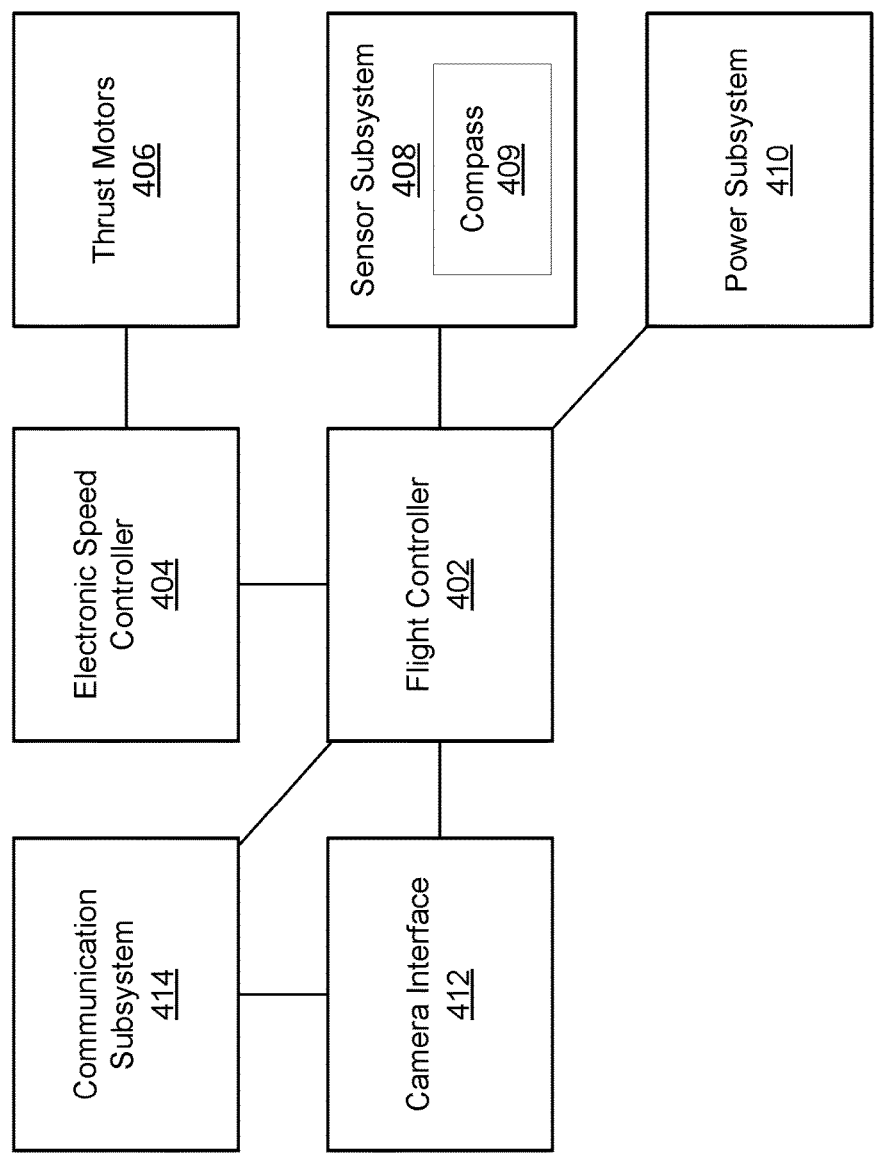
FIG. 4 illustrates a block diagram of an example unmanned aerial vehicle.

FIG. 4 illustrates a block diagram of an example unmanned aerial vehicle. The example unmanned aerial vehicle may be included in a gas detection system 100 or be separate from the gas detection system 100. The example UAV 400 includes a flight controller 402, an electronic speed controller 404, one or more thrust motors 406, a sensor (or telemetric) subsystem 408, a power subsystem 410, a camera interface 412, and a communication subsystem 414. The components may communicate directly or indirectly with each other through a data bus on the aerial vehicle 400.

The communication subsystem 414 may be a long-range Wi-Fi system. The communication subsystem 414 may include or be another wireless communication system, for example, one based on long term evolution (LTE), 3G, 4G, and/or 5G mobile communication standards. The communication subsystem 414 also may be configured with a unidirectional RC channel for communication of controls from a remote controller to the aerial vehicle 400 and a separate unidirectional channel for video downlink from the aerial vehicle 400 to the remote controller (or to a video receiver where direct video connection may be desired). The sensor subsystem 408 may include navigational components, for example, a gyroscope, accelerometer, a global positioning system (GPS) and/or a barometric sensor. The telemetric compass may also include an unmanned aerial vehicle (UAV) compass 409. The UAV compass 409 may include one or more magnetometer sensors with which it determines the orientation of the aerial vehicle 400. The power subsystem 410 may include a battery pack and/or a protection circuit module as well as a power control and/or battery management system. The camera interface 412 may interface with an image capture device or may include an integrated image capture device.

The flight controller 402 may communicate with a remote controller through the communication subsystem 416. The flight controller 402 controls the flight related operations of the aerial vehicle 400 by controlling the other components such as the electronic speed controller 404 and/or the sensor subsystem 408. The flight controller 402 can configure the flight path, the speed, the trajectory, and the position of the aerial vehicle 400 based on input from the user (for instance, via a remote controller). In addition, the flight controller 402 can configure the flight path, speed, trajectory, and position of the aerial vehicle 400 without receiving input from the user, for instance when the aerial vehicle 400 is adjacent to, within a threshold proximity of, or flying towards a virtual wall or NFZ.

The electronic speed controller 404 may be configured to interface with the thrust motors 406 (via an electronics interface) to control the speed and thrust applied to the propellers of the aerial vehicle 400. The flight controller can communicate with the camera interface 412 to capture and transmit images from an image capture device to the remote controller (or other device with a screen such as a smart phone), e.g., via the communication subsystem 414. The power subsystem 410 may be configured to manage and supply power each of the components of the aerial vehicle 400.

Embodiments described herein have other applications, for example, detection of hazardous gases in chemical plants, oil refineries, hazardous material pipelines, or any other hazardous material processing facility.

Although the detailed description contains many specifics, these should not be construed as limiting the scope of the invention but merely as illustrating different examples and aspects of the invention. It should be appreciated that the scope of the invention includes other embodiments not discussed in detail above. For example, any size or arrangement of microlenses in a microlens array can be used in this method. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

In alternate embodiments, aspects of the invention are implemented in computer hardware, firmware, software, and/or combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

What is claimed is:

1. A system for remotely detecting gas leakage from a pipe comprising:
   a first light source to emit a first outgoing light beam having a first wavelength in a mid-infrared (IR) range, the first outgoing light beam traversing an area between the system and the pipe towards a region of the pipe and having a first spot size; and
   a first light detector to detect a first incoming light beam having the first wavelength, the first incoming light beam being the first outgoing light beam reflected off of an outer surface of the region,
   a controller to execute a set of instructions configured to cause the system to:
      calculate an absorption rate by comparing an intensity of the first incoming light beam to an intensity of the first outgoing beam,
      responsive to determining the absorption rate above an absorption threshold, determine that the region has a leakage, and
      responsive to determining that the region has a leakage, regulate the first light source to emit a second outgoing light beam having the first wavelength and a second spot size less than the first spot size, the second outgoing light beam traversing the area towards the region of the pipe.

2. The system of claim 1, further comprising:
   a second light source to emit a second outgoing light beam having a second wavelength in a visible-light range, the second outgoing light beam traversing the area towards the region; and
   a second light detector to detect a second incoming light beam having the second wavelength, the second incoming light beam being the second outgoing light beam reflected off of the outer surface of the region, wherein the set of instructions are further configured to cause the system to determine a pathlength of the first outgoing light beam based on a determined phase difference between the second incoming light beam and the second outgoing light beam, responsive to determining that the region has a leakage.

3. The system of claim 1, wherein the set of instructions are further configured to calculate a concentration of the substance in the area based on the absorption rate and the pathlength.

4. The system of claim 1, wherein the first wavelength is selected based on the substance.

5. The system of claim 1, wherein the first wavelength is a value selected from 2-10 μms.

6. The system of claim 1, wherein the second wavelength is a value selected from 400-700 nms.

7. The system of claim 1, wherein the substance is selected from a group consisting of methane, ethane, propane, ethylene, acetylene, or benzene.

8. The system of claim 1, wherein the threshold is selected from 0.05-0.1 ppm·m.

9. The system of claim 1, wherein the first light source comprises focusing optics that focus the first light beam on the region.

10. The system of claim 1, further comprising collection optics to collect the first incoming light beam, the collection optics also collecting other incoming light having wavelengths different from the first wavelength.

11. The system of claim 10, further comprising an optical filter to remove the other incoming light collected by the collection optics.

12. The system of claim 11, wherein the optical filter comprises a bandpass filter having a range of 3200-3300 nm.

13. The system of claim 1 wherein the system is coupled to an unmanned aerial vehicle.

14. The system of claim 1, wherein the first outgoing light beam is modulated at a first frequency, and the first light source is controlled to emit the first outgoing light beam that continuously sweeps across a first range of wavelengths including the first wavelength.

15. The system of claim 14, wherein calculating an absorption rate further comprises:
   measuring the first incoming light beam at a first harmonic of the first frequency.

16. A method of detecting gas leakage from a pipe, comprising:
   emitting, by a first light source, a first outgoing light beam having a first wavelength in a mid-infrared (IR) range towards a region of the pipe and having a first spot size, the first outgoing light beam traversing an area between a light detector system and the pipe;
   detecting a first incoming light beam having the first wavelength, the first incoming light beam being the first outgoing light beam reflected off of an outer surface of the region;
   calculating, by a controller, an absorption rate by comparing an intensity of the first incoming light beam to an intensity of the first outgoing beam;
   responsive to determining the absorption rate above a threshold, determining that the region has a leakage; and
   responsive to determining that the region has a leakage, regulating the first light source to emit a second outgoing light beam having the first wavelength and a second spot size less than the first spot size, the second outgoing light beam traversing the area towards the region of the pipe.

17. The method of claim 16, further comprising:
   emitting, by a second light source, a second outgoing light beam having a second wavelength in the visible-light range towards the region;
   detecting, by the light detector, a second incoming light beam having the second wavelength, the second incoming light beam being the second outgoing light beam reflected off of the outer surface of the region;
   responsive to determining that the region has a leakage, determining, by the controller, a pathlength of the first outgoing light beam traversing the area by determining a response difference between the second incoming light beam and the second outgoing light beam.

18. The method of claim 16, further comprising calculating a concentration of the substance in the area based on the absorption rate and the pathlength.

19. A system for remotely detecting gas leakage from a pipe comprising:
   a first light source controlled to emit a first outgoing light beam that continuously sweeps across a first range of wavelengths at a first frequency, the range of wavelengths including a first wavelength in a mid-infrared (IR) range, and the first outgoing light beam traversing an area between the system and the pipe towards a region of the pipe; and
   a controller for executing a set of instructions configured to cause the system to:

detect a first incoming light beam having the first wavelength, the first incoming light beam being the first outgoing light beam reflected off of an outer surface of the region, calculate an absorption rate by measuring the first incoming light beam at a first harmonic of the first frequency and comparing an intensity of the first incoming light beam to an intensity of the first outgoing beam, and responsive to determining the absorption rate above a threshold, determine that the region has a leakage.

20. The system of claim 19, wherein the set of instructions are further configured to cause the system to calculate a concertation of the substance in the area based on the absorption rate and a pathlength of the first outgoing light beam.

* * * * *